(12) United States Patent
Abe et al.

(10) Patent No.: US 7,857,790 B2
(45) Date of Patent: Dec. 28, 2010

(54) INFECTION-PREVENTING GASTROSTOMY CATHETER KIT FOR GASTROSTOMY

(75) Inventors: Kazuhiro Abe, Fukuroi (JP); Nobuaki Suzuki, Fukuroi (JP); Shigeaki Funamura, Fukuroi (JP)

(73) Assignee: Tyco Healthcare Group LP, Mansfield, MA (US)

( * ) Notice: Subject to any disclaimer, the term of this patent is extended or adjusted under 35 U.S.C. 154(b) by 908 days.

(21) Appl. No.: 10/597,699

(22) PCT Filed: Feb. 3, 2005

(86) PCT No.: PCT/EP2005/001074

§ 371 (c)(1),
(2), (4) Date: May 3, 2007

(87) PCT Pub. No.: WO2005/074819

PCT Pub. Date: Aug. 18, 2005

(65) Prior Publication Data

US 2008/0039797 A1 Feb. 14, 2008

(30) Foreign Application Priority Data

Feb. 3, 2004 (JP) ............................. 2004-026348

(51) Int. Cl.
*A61M 25/01* (2006.01)
(52) U.S. Cl. ....................................... 604/171; 604/910
(58) Field of Classification Search .................. 604/270, 604/278, 539, 910, 104, 96.01, 264, 523, 604/907, 912, 915
See application file for complete search history.

(56) References Cited

U.S. PATENT DOCUMENTS 3,915,171 A * 10/1975 Shermeta ................ 604/101.05
(Continued)

FOREIGN PATENT DOCUMENTS

EP 0420486 A1 3/1991
(Continued)

OTHER PUBLICATIONS

International Preliminary Report on Patentability for International Application No. PCT/EP2005/001074 dated Aug. 17, 2006.
(Continued)

*Primary Examiner*—Nicholas D Lucchesi
*Assistant Examiner*—Quynh-Nhu H Vu
(74) *Attorney, Agent, or Firm*—Lawrence A. Chaletsky, Esq (57) ABSTRACT

An infection-preventing gastrostomy catheter kit to be used in the gastrostomy, which can pass an intragastric retainer of a catheter easily and reliably through an infection-preventing sheath by an easy maneuver, and which can reduce the diameter of the infection-preventing sheath.

The catheter kit comprises: a gastrostomy catheter 20 including a flexible, hollow PEG tube 21 reinforced with filaments 24, an deformable intragastric retainer 23 positioned at the trailing end of the PEG tube 21, and a tapered member 22 positioned at the leading end of the PEG tube 21 for retaining the leading end portion 40*a* of a guide wire 40 inserted from a leading end hole 22*a* thereof; and an infection-preventing sheath 1 including a flexible, hollow tubular body 2, and a socket member having a socket 4 positioned at the trailing end of the tubular body 2 for retaining the intragastric retainer 23, and pins 5, thereby removably sheathing the gastrostomy catheter 20. The gastrostomy catheter 20 may be provided with a housing sheath 60 for deforming and housing the intragastric retainer 23.

9 Claims, 10 Drawing Sheets

U.S. PATENT DOCUMENTS

| | | | | |
|---|---|---|---|---|
| 4,485,805 A | * | 12/1984 | Foster, Jr. | 128/898 |
| 4,758,219 A | * | 7/1988 | Sacks et al. | 604/506 |
| 4,834,725 A | | 5/1989 | Iwatschenko | |
| 5,125,897 A | | 6/1992 | Quinn et al. | |
| 5,582,165 A | * | 12/1996 | Bryan et al. | 128/207.14 |
| 5,827,242 A | | 10/1998 | Follmer et al. | |
| 5,919,231 A | | 7/1999 | Blom et al. | |
| 6,077,250 A | | 6/2000 | Snow et al. | |
| 2003/0109830 A1 | | 6/2003 | Picha et al. | |
| 2003/0229334 A1 | * | 12/2003 | Suzuki | 604/516 |

FOREIGN PATENT DOCUMENTS

| | | |
|---|---|---|
| EP | 0956878 A2 | 11/1999 |
| EP | 0980692 A1 | 2/2000 |
| EP | 1371320 A2 | 12/2003 |
| JP | 61-022868 A | 1/1986 |
| JP | 03-205062 A | 9/1991 |
| JP | 10-118189 A | 5/1998 |
| JP | 2001224694 A | 8/2001 |
| JP | 2003180840 A | 7/2003 |
| JP | 2003275324 | 9/2003 |

OTHER PUBLICATIONS

International Search Report dated Aug. 3, 2005 and Written Opinion for International Application No. PCT/EP2005/001074.

* cited by examiner

INFECTION-PREVENTING GASTROSTOMY CATHETER KIT FOR GASTROSTOMY

TECHNICAL FIELD

The present invention relates to an infection-preventing gastrostomy catheter kit for gastrostomy, to prevent a stoma infection.

BACKGROUND ART

An infection-preventing gastrostomy kit can retain a catheter without infecting a stoma when a gastrostomy operation is executed through an endoscope. This infection-preventing gastrostomy kit comprises: a catheter having a stopper at its trailing end, and fixed through an abdominal wall between the stomach cavity and the outside of the body; an over tube that is adapted to be inserted for introducing the catheter into the stomach cavity; and a soft cover disposed in the hole of the over tube. The outer circumferential wall of the leading end of the over tube on the inserted side is sheathed by folding back the trailing end of the soft cover. Another terminal end of the soft cover extrudes from the root end of the over tube (as referred to in Patent Publication 1, for example).

[Patent Publication 1]

JP-A-2003-275324 (page 1, FIG. 1 to FIG. 13)

DISCLOSURE OF THE INVENTION

According to the infection-preventing gastrostomy kit of the prior art, the catheter and the stopper experience a high resistance when they pass through the over tube. On the other hand, the patient has to accept the thick over tube that is inserted. As a result, the pains of the patient are not sufficiently relieved.

The invention has been conceived to solve the problems described above, and has as an object to provide an infection-preventing gastrostomy catheter kit to be used in the gastrostomy, which can pass an intragastric retainer of a catheter easily and reliably through an infection-preventing sheath by an easy maneuver and which can reduce the diameter of the infection-preventing sheath.

According to the invention, there is provided an infection-preventing sheath gastrostomy catheter kit comprising: a gastrostomy catheter including a flexible, hollow tube reinforced with filaments, a deformable intragastric retainer positioned at the trailing end of the tube, and a tapered member positioned at the leading end of the tube for retaining the leading end portion of a guide wire inserted from the leading end hole thereof; and an infection-preventing sheath including a flexible, hollow tubular body, and a socket member positioned at the trailing end of the tubular body for retaining the intragastric retainer, to sheathe the gastrostomy catheter removably.

There is also provided an infection-preventing sheath gastrostomy catheter kit comprising: a gastrostomy catheter including a flexible, hollow tube reinforced with filaments, a deformable intragastric retainer positioned at the trailing end of the tube, a tapered member positioned at the leading end of the tube for retaining the leading end portion of a guide wire inserted from the leading end hole thereof, and a housing sheath for deforming and housing the intragastric retainer; and an infection-preventing sheath including a flexible, hollow tubular body, and a socket member positioned at the trailing end of the tubular body for retaining the intragastric retainer, thereby to sheathe the gastrostomy catheter removably.

In this case, the infection-preventing sheath may further include a hook member disposed near the leading end portion of its inner wall for hooking the housing sheath.

The housing sheath may be made of a slender, hollow, flexible tubular body.

Moreover, the gastrostomy catheter is provided with filaments at its thick portion.

In this case, the filaments may be disposed generally parallel to the longitudinal direction of the thick portion of the gastrostomy catheter.

On the other hand, the filaments may be buried generally in parallel with the longitudinal direction of the thick portion of the gastrostomy catheter.

Moreover, the filaments may be buried at a predetermined spacing in the circumferential direction of the thick portion of the gastrostomy catheter.

On the other hand, the filaments may be made of wires of stainless steel.

The filaments may have an external diameter of about 0.2 mm.

Moreover, the intragastric retainer is foldable and deformable.

The resistance to the passage at the time when the intragastric retainer passes through the infection-preventing sheath, and an invasion to the patient and a burden on the doctor can be reduced by thinning a tubular body or an infection-preventing sheath. Moreover, the maneuver can be simplified to enable even an inexperienced doctor to operate the gastrostomy easily.

BEST MODE FOR CARRYING OUT THE INVENTION

Embodiment 1

Figure 1:
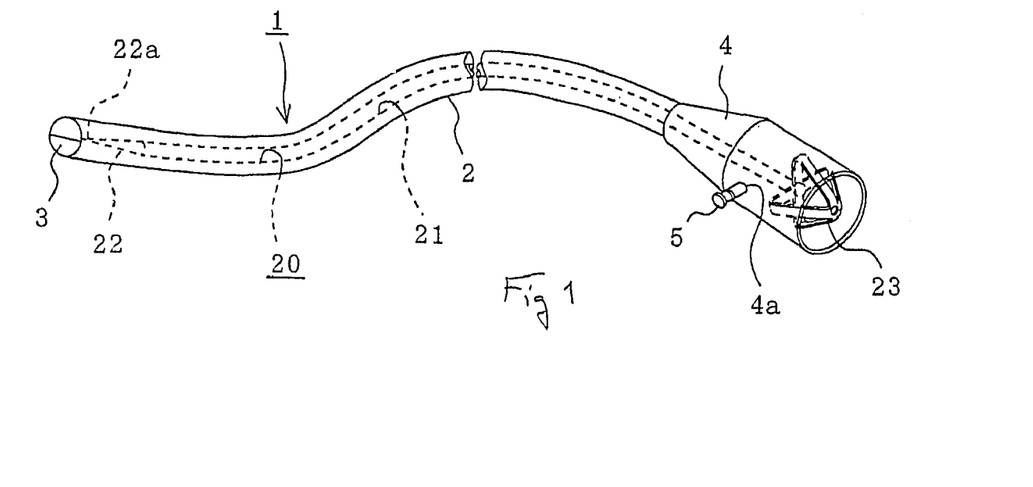
FIG. 1 is a perspective view of an infection-preventing sheath according to Embodiment 1 of the Invention.
Figure 2:
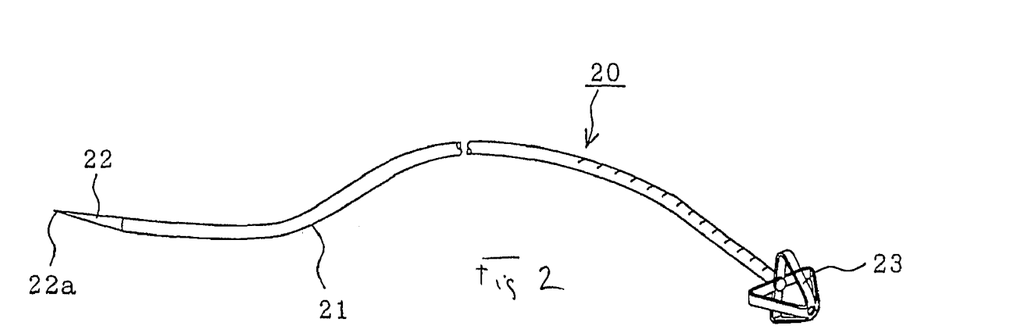
FIG. 2 is a perspective view of a catheter for gastrostomy.

FIG. 1 is a perspective view showing an inspection preventing gastrostomy catheter kit to be used in an inspection-preventing gastrostomy method (as will be called the "PEG method"), and FIG. 2 is a perspective view showing a gastrostomy catheter (as will be called the "PEG catheter"). An inspection-preventing sheath 1 removably sheathes the PEG catheter 20 (which will be described in detail) from its outer side, thereby preventing the PEG catheter 20 from being contaminated with bacteria in an oral cavity, a pharynx or a larynx. The inspection-preventing sheath 1 includes a slender, hollow flexible tubular body 2, which can also be called the "flexible tubular member" or "flexible tube". A leading end thin film 3, which is cut at its leading end, is fixed to the leading end of the tubular body 2. A hollow socket 4 is disposed at the trailing end of the tubular body 2. The socket 4 has a generally frusto-conical portion and a generally cylindrical portion leading to an end portion on the radially larger side of the frusto-conical portion. The socket 4 is formed to have its radially smaller end portion mouth adhered to the trailing end of the tubular body 2 with an adhesive or the like, or fused to or molded integrally with the same. The opposed portions of the cylindrical portion of the socket 4 have drilled bearing holes 4a, in which pins 5 are to be inserted. Here, the cylindrical portion may be constructed to sheathe an intragastric retainer, or may be constructed not to sheath the same.

The tubular body 2 is made of a flexible, strong material of polyvinyl chloride that has gas-tightness, water-tightness and no shrinkage in the longitudinal direction. The tubular body 2 is preferably cylindrical, but may alternatively have a shape of a flattened section, such as an elliptical shape. The socket 4 is made of a hard material such as polycarbonate, and the leading end film 3 is made of a thin sheet of polyvinyl chloride or the like.

The PEG catheter 20 is constructed by continuously integrating: a slender, hollow PEG tube 21; a tapered member 22 disposed at the leading end of the PEG tube 21, tapered generally conically toward its leading end and provided with a hole 22a leading to the hollow inside of the PEG tube 21; and an intragastric retainer 23 positioned at the trailing end. The PEG tube 21 is made of a resilient material such as polyurethane. The tapered member 22 is made of a relatively hard material such as polypropylene, and the intragastric retainer 23 is made of a flexible material such as polyurethane having such an elasticity deformable by an external force and restored to its original shape when the external force disappears.

Figures 3A, 3B:
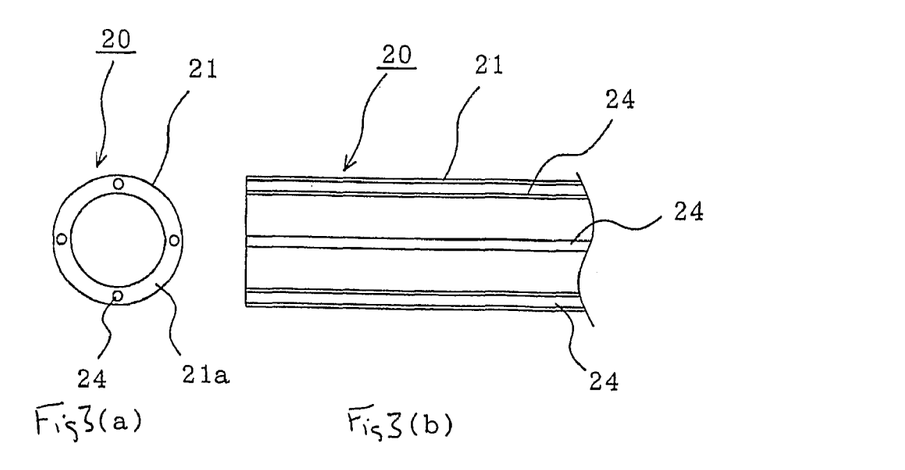
FIGS. 3(a)-(b) present a sectional view and a side view of an essential portion of FIG. 2.

The PEG tube 21 is provided, as shown in FIGS. 3(a)-(b), with a plurality of hardly extensible filaments 24 in the longitudinal direction of a thick portion 21a. More specifically, the filaments 24 are arrayed at a predetermined interval along the circumferential direction of the thick portion 21a and generally in parallel in the longitudinal direction. Thus, extension of the PEG catheter 20 is suppressed when the PEG catheter 20 is pulled with a guide wire 40 retained in the tapered member 22. In this case, the filaments 24 need not be buried and fixed integrally with the thick portion 21a but may also be arrayed along the surface of the thick portion 21a. The yarns of the filaments 24 may also be such wires of stainless steel, for example, having an external diameter of about 0.2 mm, so that they can be cut with scissors. The yarns of the filaments 24 may also be cotton yarns.

Figures 4A, 4B, 4C:
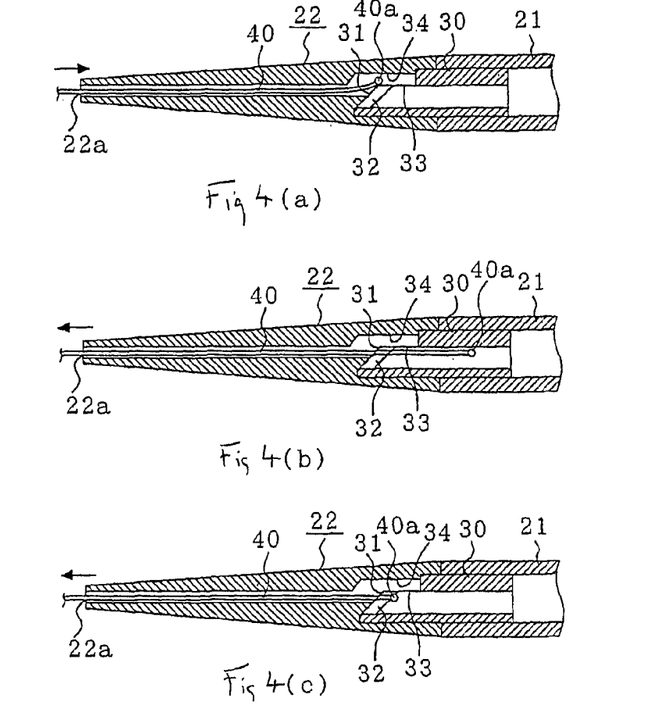
FIGS. 4(a)-(c) present diagrams to explain the steps for views of FIG. 2.

As shown in FIGS. 4(a)-(c), the hole 22a, which is formed at the leading end of the tapered member 22 of the PEG catheter 20, has a diameter made large enough to accept the head portion 40a formed at the leading end of the guide wire 40, so that the guide wire 40 can be inserted from the hole 22a into the tapered member 22.

This tapered member 22 is provided, on the inner side of its diametrically large end portion, with a step portion, on which a connector 30 is fitted. At this fitted portion, the tapered member 22 and the connector 30 are fixed by adhering or welding.

Figure 5:
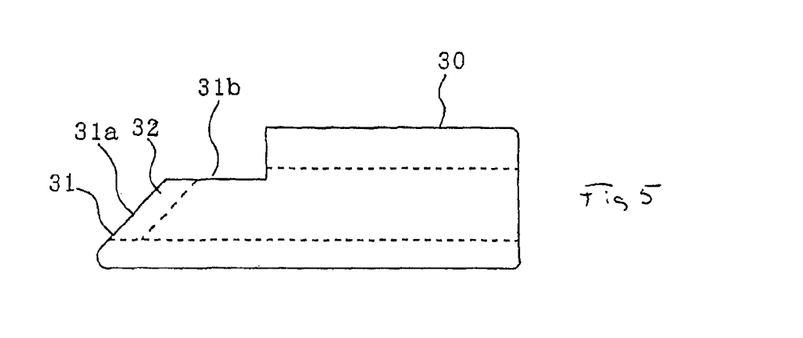
FIG. 5 is a side view of an essential portion of FIG. 4.
Figure 6:
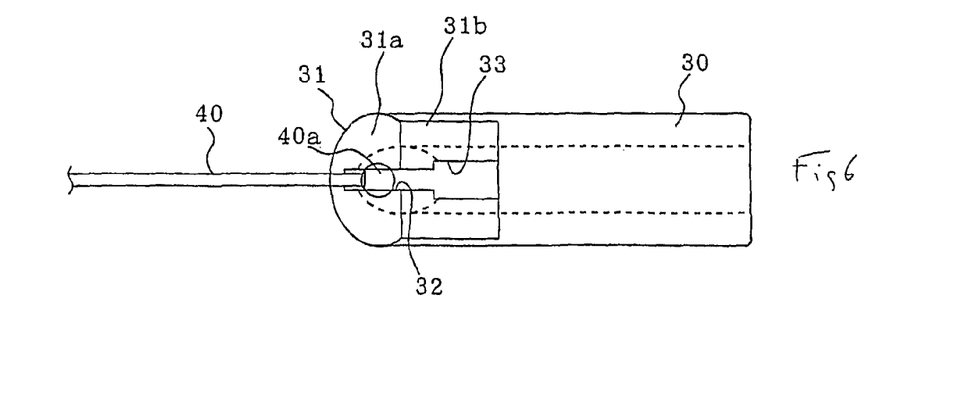
FIG. 6 is a top plan view of FIG. 5.

As shown in FIG. 5 and FIG. 6, the connector 30 positioned in the tapered member 22 is made hollow to have a cylindrical hole. The connector 30 per se has a generally cylindrical shape.

At the leading end of the connector 30, a retaining member 31 is made integral with the connector 30. The retaining member 31 extends obliquely of the axial direction from the leading end of the connector 30 to form a slope 31a, and turns midway into parallel to the axial direction to form an upper flat face 31b.

In the retaining member 31, moreover, there is formed a first narrower groove 32, which extends from the lower portion of the slope 31a to the vicinity of the central portion of the upper flat face 31b. In this upper flat face 31b of the retaining member 31, there is also formed a second wider groove 33, which merges into the first groove 32 and has a width made large enough to pass the head portion 40a of the guide wire 40 therethrough.

In that upper portion of the inside of the tapered member 22, in which the retaining member 31 is to be positioned, there is formed a space 34, which is large enough to pass the head portion 40a of the guide wire 40 therethrough, as shown in FIG. 4.

The intragastric retainer 23 positioned at the trailing end of the PEG catheter 2 0 is constructed of four finger-shaped members, which are connected in a cross shape at their leading ends and at their trailing ends and can be freely folded to be bent and extended, with the pins 5 abutting against the outer side of the root portion, as shown in FIG. 2.

Figure 7:
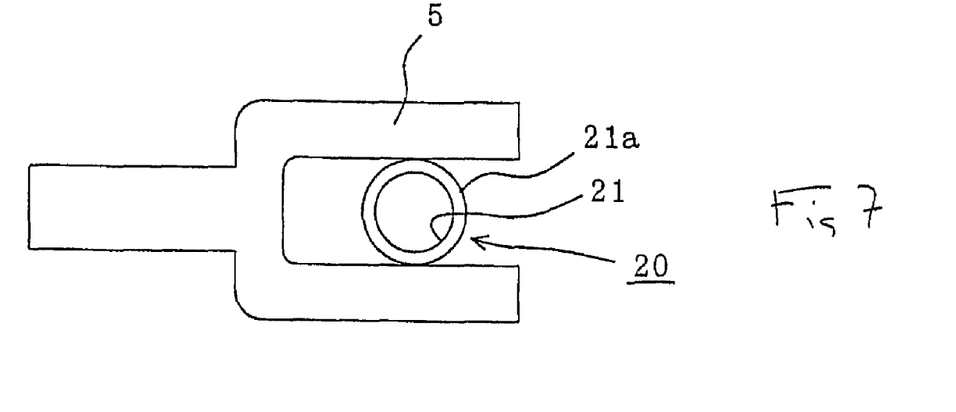
FIG. 7 is an explanatory view of an essential portion of FIG. 1.

As shown in FIG. 7, for example, the pins 5 are formed into a bifurcated shape. When the pins 5 are inserted into the bearing holes 4a, their two branches clamp the surface of the PEG tube 21 of the PEG catheter 20. When the PEG catheter 20 is pulled in the direction of the taper member 22, the pins 5 abut against the outer side face of the root portion of the intragastric retainer 23 to prevent the PEG catheter 20 from moving in the direction of the tapered member 22.

The length of the infection-preventing sheath 1, that is, the total length of the tubular body 2 and the socket 4, is slightly larger than the length of the PEG catheter 20, that is, the total length of the tapered member 22, the PEG tube 21 and the intragastric retainer 23. Moreover, the internal diameter of the tubular body 2 is larger than the external diameter of the PEG tube 21 but smaller than the diameter or the transverse width of the intragastric retainer 23.

Depending on the material to be used for the intragastric retainer 23, the internal diameter of the tubular body 2 may be made larger than the diameter of the intragastric retainer 23. In any event, it is sufficient that the PEG catheter 20 pass together with the intragastric retainer 23 (in the folded state or in the original shape) through the tubular body 2 of the infection-preventing sheath 1. Here, a jelly or another lubricant may be applied to the inner face of the tubular body 2.

The actions with respect to Embodiment 1 thus constructed are described below. The mode of embodiment to be described is called the "pull method". The PEG method is generally executed by an operator, an endoscopist doctor and one or two nurses.

Figure 8:
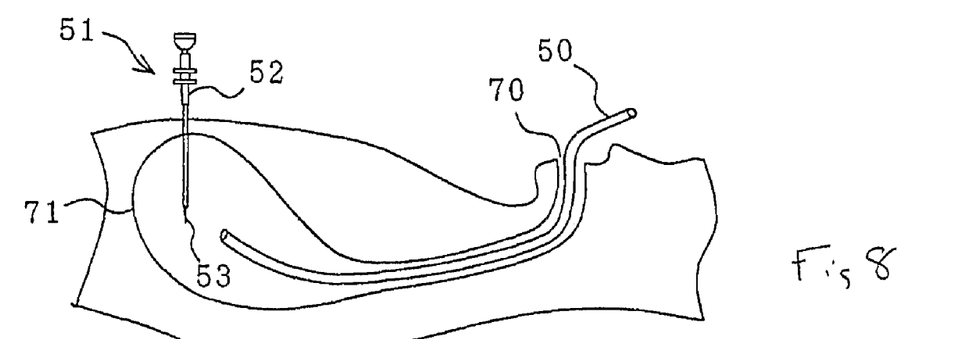
FIG. 8 is a diagram for explaining the steps of a gastrostomy method according to Embodiment 1.

First of all, as shown in FIG. 8, an endoscope 50 is inserted from the mouth 70 of a patient lying on his or her back into a stomach 71, and air is blown through the endoscope 50 into the stomach 71 to expand the stomach 71, thereby bringing the stomach wall and the peritoneum into close contact with each other. Then, the portion to be needled is determined and sufficiently disinfected, and its vicinity is locally anesthetized. Next, the skin of the portion to be needled is cut about 1 cm, and a sheathed needle 51 is inserted into the cut portion.

This sheathed needle 51 is composed of a circular outer cylinder 52 and a needle 53 having a sharpened leading end. The outer cylinder 52 is made hollow, and the needle 53 slightly protrudes at its leading end from the leading end of the outer cylinder 52. The sharpened leading end of the needle 53 pierces into the abdominal wall, the peritoneum and the stomach wall so far that the leading end portion of the outer cylinder 52 penetrates into the abdominal wall, the peritoneum and the stomach wall.

Figure 9:
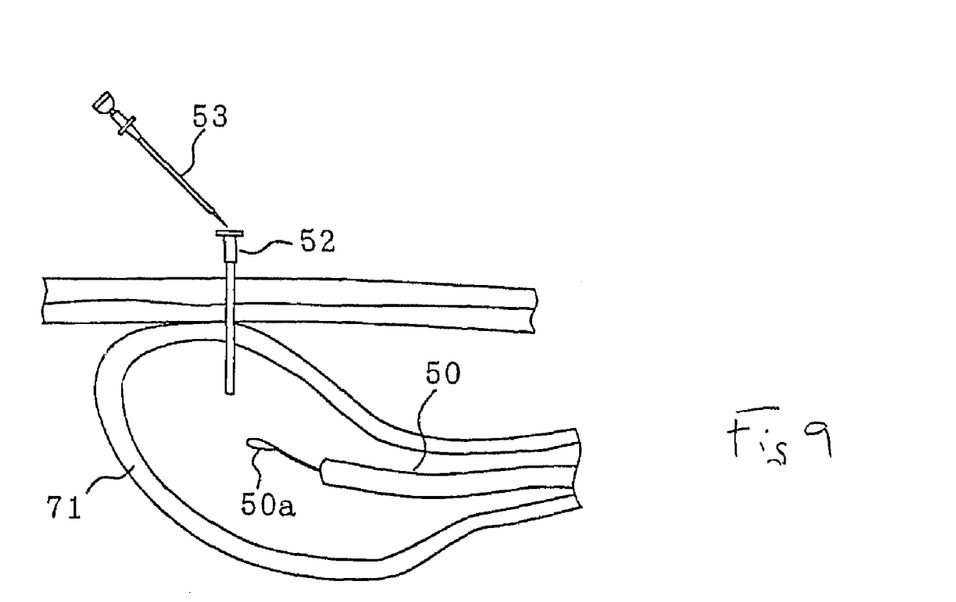
FIG. 9 is a diagram for explaining the steps of the gastrostomy method according to Embodiment 1.

Next, as shown in FIG. 9, the needle 53 is extracted from the outer cylinder 52 while leaving the leading end portion of the outer cylinder 52 needled from the abdominal wall to the stomach wall. Moreover, the leading end of a snare forceps 50a is extended from the leading end of the endoscope 50 in the stomach 71.

Figure 10:
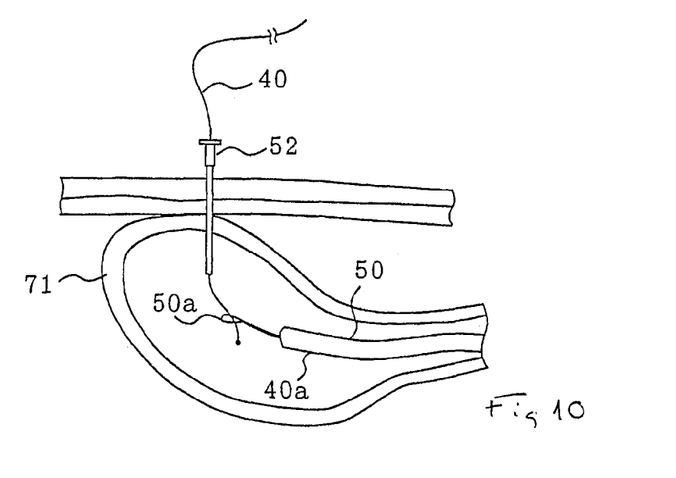
FIG. 10 is a diagram for explaining the steps of the gastrostomy method according to Embodiment 1.

Next, the guide wire 40 having the ball-shaped head portion 40a at its leading end is inserted from the outside through the outer cylinder 52 into the stomach 71, as shown in FIG. 10.

The leading end portion of the guide wire 40 inserted into the stomach 71 is gripped by the snare forceps 50a and is pulled out to the outside of the oral cavity until it is ungripped from the snare forceps 50a. At this time, the trailing end of the guide wire 40 is held outside of the outer cylinder 52.

Moreover, the PEG catheter 20 is inserted on the side of the tapered member 22 from the open side of the socket 4 of the infection-preventing sheath 1 into the tubular body 2 and is sheathed from the tapered member 22 of the PEG catheter 20 to the intragastric retainer 23 with the infection-preventing sheath 1 (as referred to FIG. 1). At the manufacture time or before the operation, the PEG catheter 20 may also be sheathed in advance with the infection-preventing sheath 1.

Figure 11:
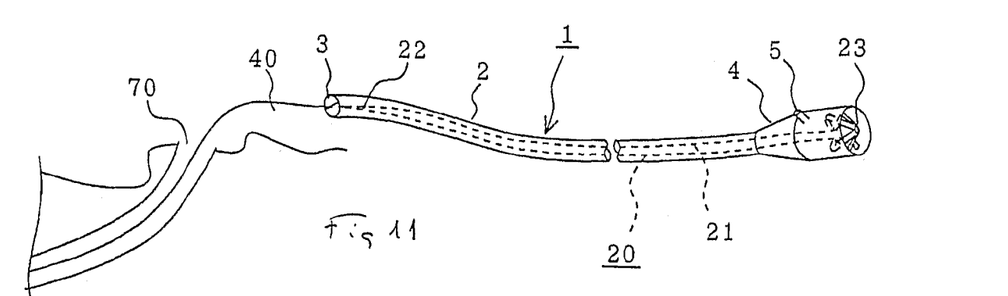
FIG. 11 is a diagram for explaining the steps of the gastrostomy method according to Embodiment 1.

Thus, the leading end of the tapered member 22 is slightly extracted from the leading end film 3 of the leading end of the tubular body 2 to the outside, and the leading end of the guide wire 40 extracted from the oral cavity of the patient is pulled from the hole 22 in the leading end of the tapered member 22 into the tapered member 22. The guide wire 40 is retained at its head portion 40a on the connector 30 of the tapered member 22. As shown in FIG. 11, moreover, the pins 5 are inserted into the bearing holes 4a formed in the socket 4 of the infection-preventing sheath 1 thereby to retain the intragastric retainer 23 in the socket 4.

Shown below are the steps to retain the head portion 40a of the guide wire 40 and the tapered member 22 of the PEG catheter 20. As the guide wire 40 is inserted from the leading end hole 22a of the tapered member 22 into the tapered member 22, the ball-shaped head portion 40a at the leading end of the guide wire 40 rides on the slope 31a of the obliquely arranged retaining member 31 and reaches the inside space 34 of the tapered member 22 as shown in FIG. 4(a).

As the guide wire 40 is further inserted, the head portion 40a of the guide wire 40 drops at the upper flat face 31b of the retaining member 31 into the wider groove 33 and enters the narrower groove 32 as shown in FIG. 4(b).

If the guide wire 40 extending from the abdomen of the patient through the outer cylinder 52 to the outside is pulled in this state from the outside, the head portion 40a at the leading end portion of the guide wire 40 is retained in the stomach by the tapered member 22 at the leading end of the PEG catheter 20 as shown in FIG. 4(c).

When the guide wire 40 is pulled, the pulling force acts at the portion of the tapered member 22, and the PEG catheter 20 and the infection-preventing sheath 1 are pulled, while the tapered member 22 and the PEG tube 21 are sheathed with the infection-preventing sheath 1, into the stomach 71 through the oral cavity, the larynx, the pharynx and esophagus.

At this time, the hardly extensible filaments 24 are fixed in the longitudinal direction of the thick outer circumferential portion 21a of the PEG tube 21. As a result, the PEG catheter 20 is not extended, even if the portion of the tapered member 22 of the PEG catheter 20 is pulled by the guide wire 40.

Figure 12:
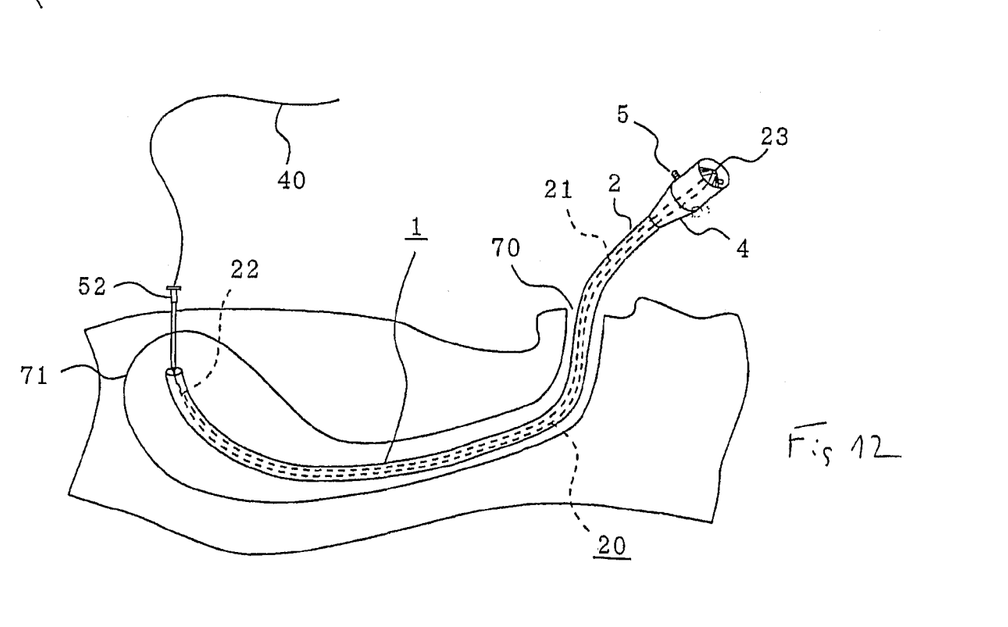
FIG. 12 is a diagram for explaining the steps of the gastrostomy method according Embodiment 1.

Thus, as shown in FIG. 12, the tapered member 22 of the PEG catheter 20 either abuts against the leading end of the outer cylinder 52 or reaches the vicinity of the outer cylinder 52. This abutment or reach can also be confirmed by using the endoscope. In this state, the intragastric retainer 23 at the trailing end of the PEG catheter 20 and the socket 4 at the trailing end of the infection-preventing sheath 1 are still outside of the mouth 71 of the patient.

Figure 13:
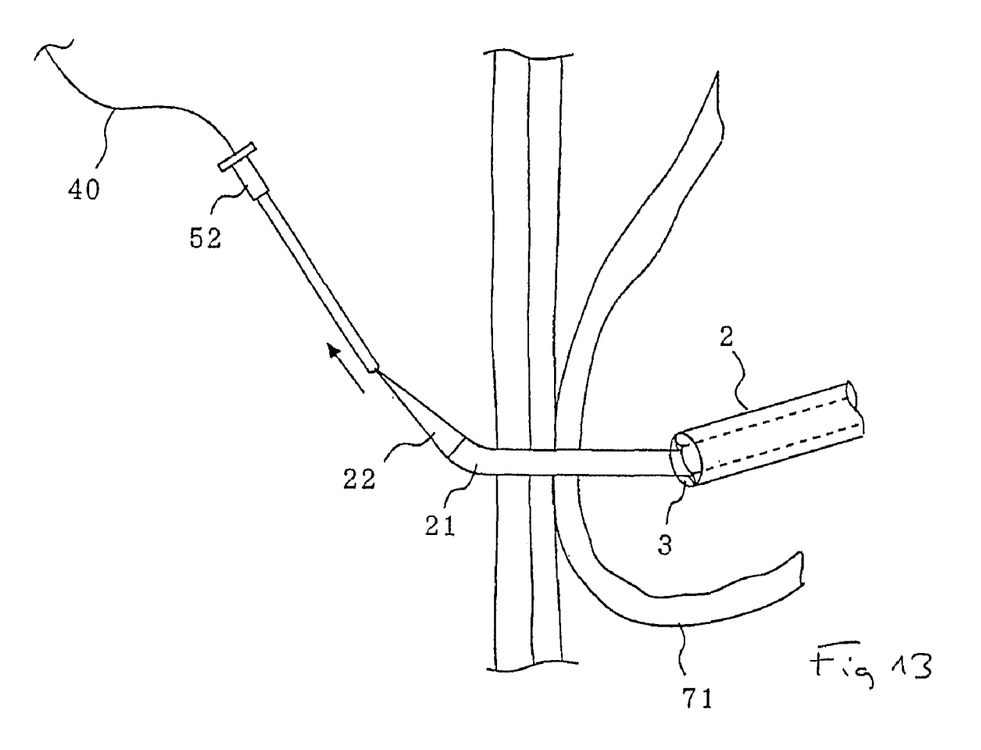
FIG. 13 is a diagram for explaining the steps of the gastrostomy method according Embodiment 1.
Figure 14:
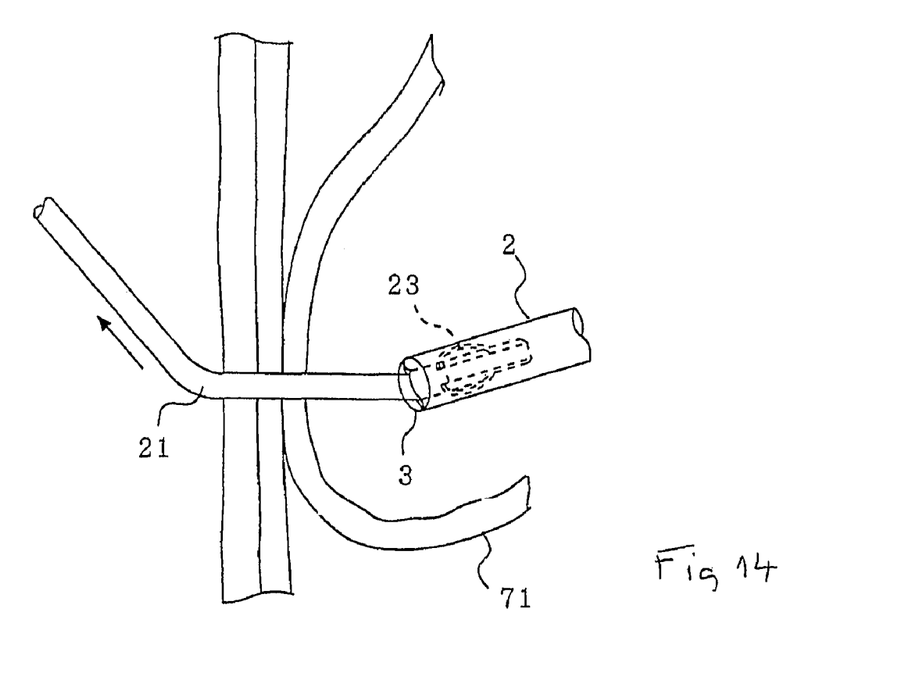
FIG. 14 is a diagram for explaining the steps of the gastrostomy method according Embodiment 1.

Then, the pins 5 are pulled out from the bearing holes 4a to release the intragastric retainer 23, and the guide wire 40 is further pulled out while extracting the outer cylinder 52 from the stomach wall and the abdominal wall, as shown in FIG. 13. As a result, the tapered member 22 connected to the guide wire 40 and the PEG tube 21 connected to the tapered member 22 pass through the leading end film 3 at the leading end of the tubular body 2 and appear in the stomach 71. At the trailing end of the tubular body 2, the flexible intragastric retainer 23 is pulled in the folded sate into the tubular body 2 so that it advances toward the abdomen. While the guide wire 40 is being thus pulled to the outside of patient, the socket 4 extracted from the mouth 71 of the patient is gripped by the hand of the endoscopist so that the infection-preventing sheath 1 may not be pulled into the body of the patient. As the guide wire 40 is further pulled, the tapered member 22 and the PEG tube 21 are pulled to the outside through the holes in the stomach wall and the abdominal wall, as shown in FIG. 14.

Figure 15:
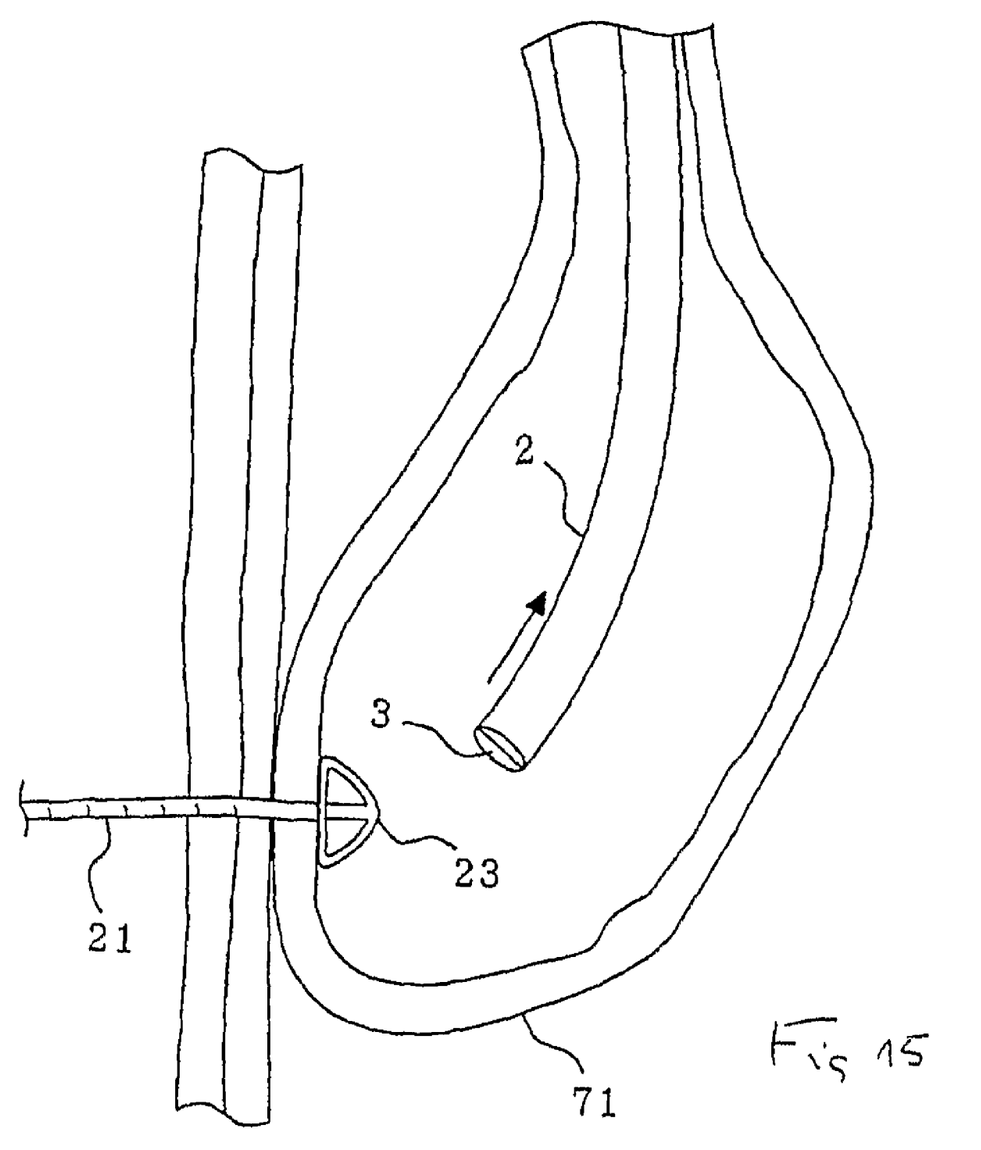
FIG. 15 is a diagram for explaining the steps of the gastrostomy method according Embodiment 1.

When the intragastric retainer 23 comes out from the leading end film 3 of the tubular body 2 and appears in the stomach 71, it restores its original shape having the four extended filaments, as shown in FIG. 15, to abut against the stomach wall. This abutment of the intragastric retainer 23 against the stomach wall may be confirmed, if necessary, by the endoscope 50. After this, the tubular body 2 is extracted from the mouth 70 of the patient to the outside.

The PEG tube 21 thus extracted to the outside of the patient's body is cut to a suitable length, and a (not-shown) adapter for injecting nutriments is connected to the cut portion. Moreover, the PEG tube 21 is fixed on the patient's body with a suitable fixing tool, thus ending the operation of the PEG method.

Thus, the outer surfaces of the guide wire 40 and the tubular body 2 having passed through the oral cavity, the larynx and the pharynx may be contaminated with the bacteria sticking to the oral cavity, the larynx and the pharynx. However, the guide wire 40 is pulled out of the body of the patient through the outer cylinder 52 so that those portions of the stomach wall and the abdominal wall, which are to be subjected to the gastrostomy, are not contaminated by the guide wire 40. Moreover, the PEG catheter 20 is pushed, while being covered all over with the infection-preventing sheath 1, through the oral cavity, the pharynx and the larynx into the stomach and is pulled from the tubular body 2 through the leading end film 3 in the stomach, so that the PEG catheter 20 is not contaminated with the bacteria. Therefore, the portions for the gastrostomy are not contaminated with the bacteria, even if the tapered member 22 and the PEG tube 21 contact those portions when they are pulled out from the body. On the other hand, the tubular body 2 having its surface contaminated with the bacteria is extracted from the mouth of the patient to the outside, so that the portions for the gastrostomy are not contaminated with the infection-preventing sheath 1 including the tubular body 2. As a result, those portions can be prevented in advance from any contamination.

In the push method as well, the PEG catheter 20 sheathed with the infection-preventing sheath 1 is pushed into the stomach so that the portions for the gastrostomy can be effectively prevented from being contaminated with the bacteria.

Moreover, the PEG tube 21 is longitudinally provided with the hardly extensible filaments 24 for reinforcement. As a result, the PEG catheter 20 is not extended, although pulled at the portion of the tapered member 22, and it is sufficient at the retaining time that the tapered member 22 is retained only once.

Embodiment 2

Figure 16:
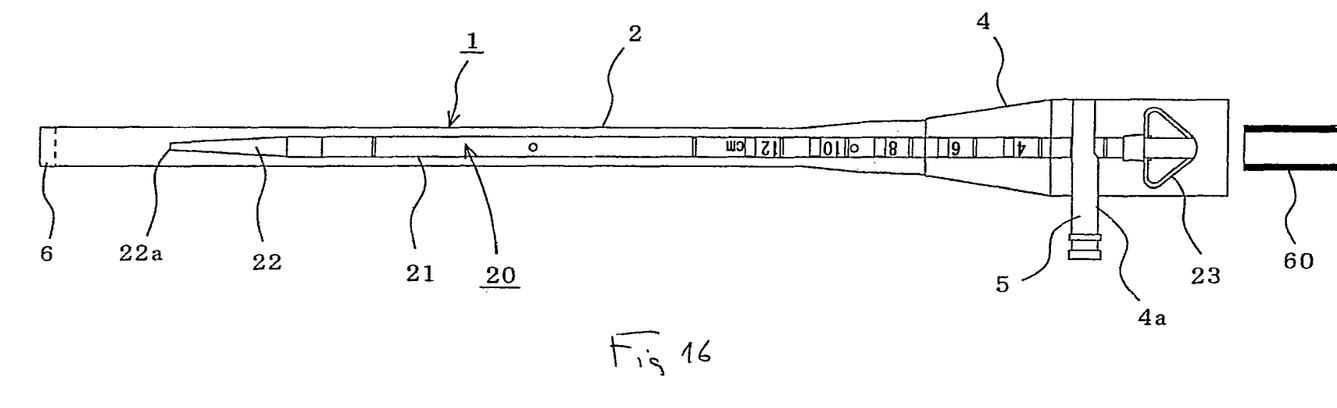
FIG. 16 is a side elevation showing an infection-preventing gastrostomy catheter kit according to Embodiment 2 of the invention.
Figure 17:
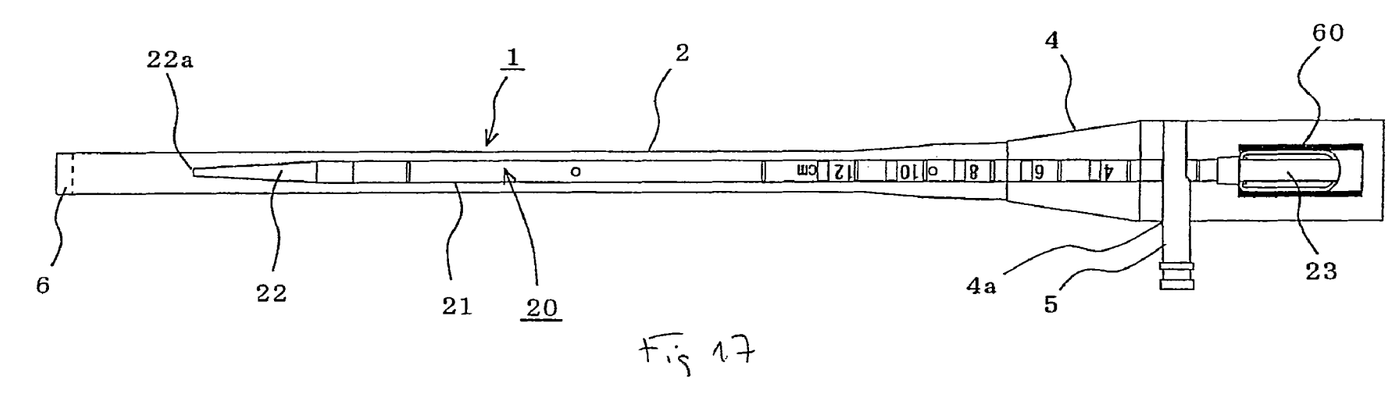
FIG. 17 is a diagram for explaining the steps of FIG. 16.
Figure 18:
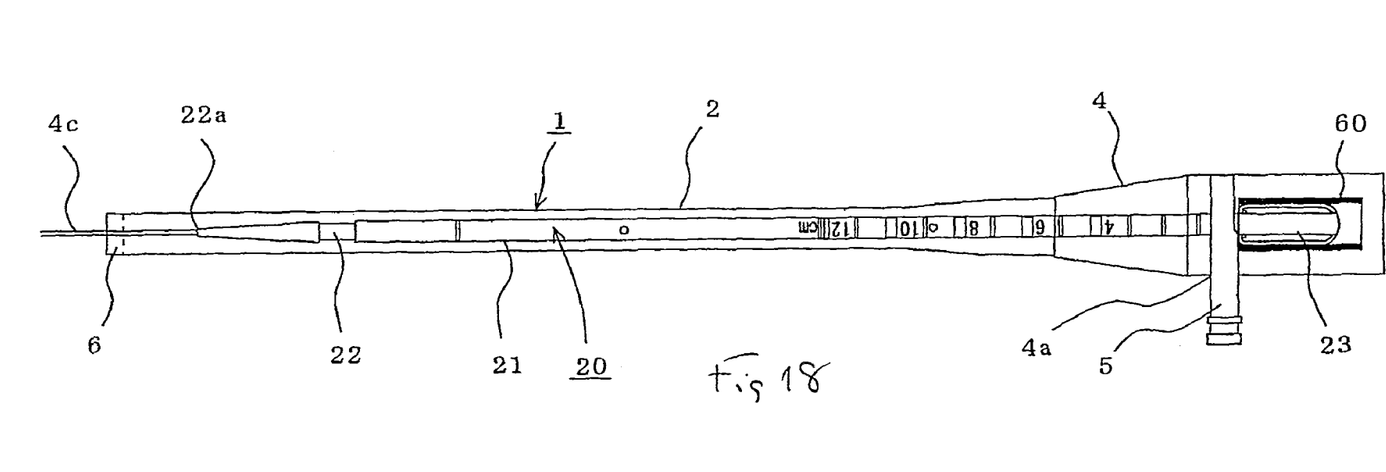
FIG. 18 is a diagram for explaining the steps of FIG. 16.

FIG. 16 is an explanatory view showing an infection-preventing catheter kit for the gastrostomy according to Embodiment 2, and FIG. 17 and FIG. 18 are explanatory views for explaining the actions of the kit. In this mode of embodiment, the infection-preventing gastrostomy catheter kid is provided with a housing sheath 60 for folding and housing the intragastric retainer 23 of the PEG catheter 20 preliminarily in an extended state, so that the intragastric retainer 23 may be able to pass through the infection-preventing sheath 1.

The remaining constructions are substantially similar to those of the case of Embodiment 1, and their description is omitted by designating the same portions as those of Embodiment 1 by the common reference numerals.

As shown in FIG. 16, the housing sheath 60 is formed to have a flexible tubular body having an outer diameter slightly smaller than the internal diameter of the tubular body 2 of the infection-preventing sheath 1.

As shown in FIG. 17 and FIG. 18, the intragastric retainer 23 is housed in advance in the folded and extended state so that it may be able to pass in that state through the infection-preventing sheath 1.

The infection-preventing sheath 1 is provided, on the inner wall of its leading end side, with a hook member 6, which is diametrically reduced to have an internal diameter smaller than that of the tubular body 2. When the intragastric retainer 23 of the PEG catheter 20 comes out of the leading end portion of the tubular body 2 of the infection-preventing sheath 1, the hook member 6 hooks only the housing sheath 60, so that it can pull out only the intragastric retainer 23 while leaving the housing sheath 60 in the infection-preventing sheath 1.

Figure 19:
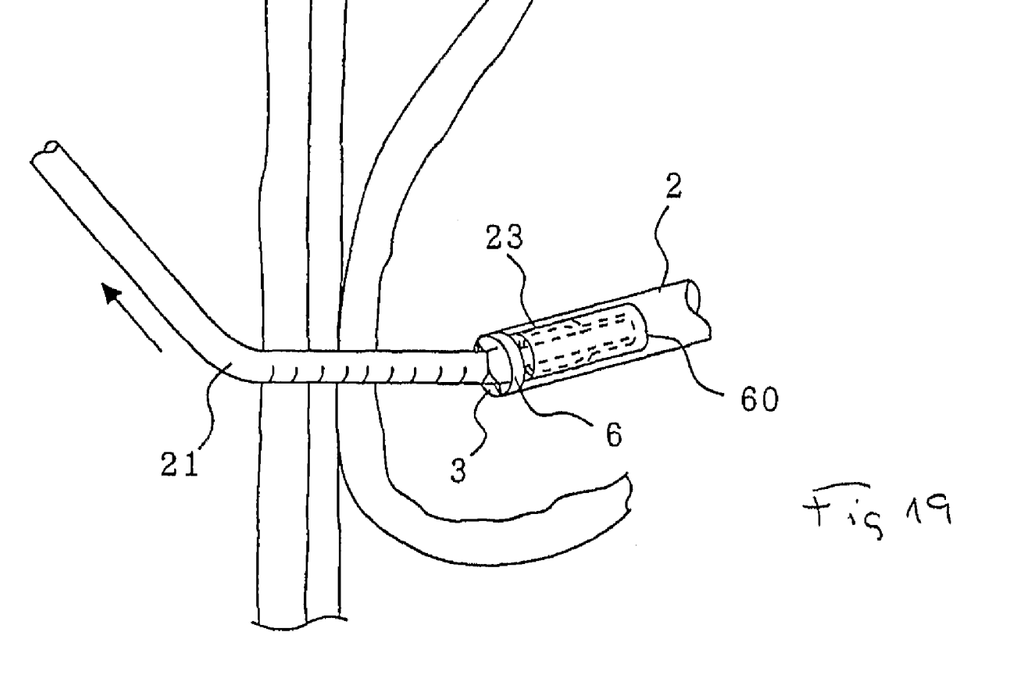
FIG. 19 is a diagram for explaining the steps of a gastrostomy method according to Embodiment 2.

Below are described the steps for the invention thus constructed. As the pins 5 shown in FIG. 18 are pulled out to extract the PEG catheter 20 from the infection-preventing sheath 1 with the guide wire 40, the PEG catheter 20 is moved toward its leading end portion along the inner wall of the infection-preventing sheath 1. Then, the intragastric retainer 23 is moved, while being folded and housed in the housing sheath 60, together with the PEG catheter 20 along the inner wall of the infection-preventing sheath 1. When the housing sheath 60 comes to the position of the hook member 6, as shown in FIG. 19, only the housing sheath 60 is hooked by the hook member 6. As a result, the intragastric retainer 23 is pulled out from the leading end portion of the infection-preventing sheath 1 while leaving the housing sheath 60 in the tubular body 2 of the infection-preventing sheath 1, so that the intragastric retainer 23 restores its original shape in the stomach.

The remaining actions are substantially similar to those of the case of Embodiment 1, and their description is omitted.

In the aforementioned case, the hook member 6 is not disposed on the inner wall of the infection-preventing sheath 1, but the housing sheath 60 may be extracted together with the intragastric retainer 23 into the stomach, so that the intragastric retainer 23 may be extracted from the housing sheath 60 by pinching and pulling the thread engaging with the housing sheath 60, by means of the snare.

Alternatively, the hook member 6 is not either disposed on the inner wall of the infection-preventing sheath 1, but the housing sheath 60 may be extracted together with the intragastric retainer 23, and the intragastric retainer 23 may then be removed directly from the housing sheath 60 by means of the snare.

In this embodiment, the intragastric retainer 23 is folded and extended in advance and housed in the housing sheath 60 so that it can pass through the infection-preventing sheath 1. As a result, the passage resistance in the infection-preventing sheath 1 can be reduced to make the infection-preventing sheath 1 thinner.

The invention claimed is:

1. An infection-preventing sheath gastrostomy catheter kit comprising: a gastrostomy catheter including a flexible, hollow tube reinforced with filaments, a deformable intragastric retainer positioned at the trailing end of said tube, a tapered member positioned at the leading end of said tube for retaining the leading end portiion of a guide wire inserted from the leading end hole thereof, and a housing sheath for deforming and housing said intragastric retainer; and an infection-preventing sheath including a flexible, hollow tabular body, and a socket member positioned at the trailing end of said tubular body for retaining said intragastric retainer, to removably sheathe said gastrostomy catheter and wherein said infection-preventing sheath further includes a hook member disposed near the leading end portion of its inner wall for hooking said housing sheath; whereby the intragastric retainer is pulled out while leaving the housing sheath in the infection-preventing sheath.

2. An infection-preventing sheath gastrostomy catheter kit according to claim 1, wherein said housing sheath is made of a slender, hollow, flexible tubular body.

3. An infection-preventing sheath gastrostomy catheter kit according to claim 1, wherein the gastrostomy catheter is provided with filaments at its thick portion.

4. An infection-preventing sheath gastrostomy catheter kit according to claim 3, wherein said filaments are disposed generally in parallel with the longitudinal direction of the thick portion of the gastrostomy catheter.

5. An infection-preventing sheath gastrostomy catheter kit according to claim 4, wherein said filaments are buried generally in parallel with the longitudinal direction of the thick portion of the gastrostomy catheter.

6. An infection-preventing sheath gastrostomy catheter kit according to claim 3, wherein said filaments are buried at a predetermined spacing in the circumferential direction of the thick portion of the gastrostomy catheter.

7. An infection-preventing sheath gastrostomy catheter kit according to claim 1, wherein said filaments are made of wires of stainless steel.

8. An infection-preventing sheath gastrostomy catheter kit according to claim 1, wherein the filaments have an external diameter of about 0.2 ram.

9. An infection-preventing sheath gastrostomy catheter kit according to claim 1, wherein the intragastric retainer is made foldable and deformable.

* * * * *